US005853551A

United States Patent [19]

Boucot et al.

[11] Patent Number: 5,853,551

[45] Date of Patent: Dec. 29, 1998

[54] PROCESS FOR THE SEPARATION OF ALPHA-OLEFINS BY DISTILLATION OF AN EFFLUENT COMPRISING ETHYLENE AND 1-BUTENE

[75] Inventors: Pierre Boucot, Ternay; Jean-Alain Chodorge, Antony; Alain Forestiere, Vernaison; Yves Glaize, Saint Symphorien D'Ozon; François Hughes, Vernaison, all of France

[73] Assignee: Institut Francais du Petrole, France

[21] Appl. No.: 720,384

[22] Filed: Jul. 23, 1996

[30] Foreign Application Priority Data

Jul. 24, 1995 [FR] France .................................. 95 09059

[51] Int. Cl.[6] ................................ B01D 3/34; B01D 3/14

[52] U.S. Cl. ................................ 203/70; 203/75; 203/82

[58] Field of Search .................................. 203/70, 75, 82

[56] References Cited

U.S. PATENT DOCUMENTS

| | | | |
|---|---|---|---|
| 2,775,103 | 12/1956 | Koble et al. | 62/123 |
| 4,542,251 | 9/1985 | Miller | 585/530 |
| 4,589,957 | 5/1986 | Sherk et al. | 203/75 |

*Primary Examiner*—Tae Yoon
*Attorney, Agent, or Firm*—Millen, White, Zelano & Branigan, P.C.

[57] ABSTRACT

The invention concerns a process for the separation of a mixture comprising ethylene, 1-butene, alpha-olefins containing at least 6 carbon atoms per molecule and possibly heavier hydrocarbon products, the ethylene content of the mixture being in the range 30% to 70% by weight, in which separation is effected in a distillation zone to obtain an overhead fraction comprising the major portion of the ethylene present in the mixture and between 0% and 100% by weight of the 1-butene present in the mixture, the process being characterized in that the zone is also supplied with supplemental 1-butene in an amount in the range 1 to 40 times the quantity (by weight) of 1-butene present in the mixture. In a preferred implementation of the process of the invention, the mixture originates form a homogenous liquid phase ethylene oligomerisation zone.

21 Claims, No Drawings

PROCESS FOR THE SEPARATION OF ALPHA-OLEFINS BY DISTILLATION OF AN EFFLUENT COMPRISING ETHYLENE AND 1-BUTENE

BACKGROUND OF THE INVENTION

The present invention concerns an improved industrial process for the separation of a mixture comprising ethylene, 1-butene, alpha-olefins containing at least 6 carbon atoms per molecule and possibly heavier hydrocarbon products, the ethylene content of the mixture being in the range 30% to 70% by weight. In a preferred implementation of the process of the present invention, the mixture originates from a homogeneous liquid phase ethylene oligomerisation zone and comprises unreacted ethylene, 1-butene, 1-hexene, 1-octene, olefins containing at least 10 carbon atoms per molecule, inhibited catalyst and oligomerisation solvent.

Ethylene oligomerisation is usually carried out in a generally homogeneous catalytic liquid phase process in the presence or otherwise of a solvent, using a Ziegler type catalyst which generally comprises a compound of a metal such as titanium, chromium, zirconium and an organoaluminium compound, at a temperature in the range 100° C. to 200° C. and at a pressure in the range 0.5 MPa to 20 MPa. In a preferred implementation of the process of the present invention, the separation process follows an oligomerisation process in the presence of a solvent.

The effluent from the ethylene oligomerisation step comprises unconverted ethylene and alpha-olefins, mainly 1-butene, 1-hexene, 1-octene, the oligomerisation solvent and $C_{10}^+$ alpha-olefins (i.e., containing at least 10 carbon atoms per molecule). The effluent also includes catalyst. At the outlet to the oligomerisation step, the catalyst is deactivated by any compound which is known to the skilled person to inhibit an oligomerisation catalyst. The compound is generally an amine, preferably a long chain amine, i.e., containing at least six carbon atoms per molecule. Thus the feed to be separated preferably comprises essentially unconverted ethylene, 1-butene, 1-hexene, 1-octene, oligomerisation solvent, the compound resulting from deactivation of the catalyst by the inhibitor, which for simplicity will be referred to as inhibited catalyst, and $C_{10}^+$ alpha-olefins.

The separation of ethylene from alpha-olefins such as 1-butene, 1-hexene and 1-octene, and from the solvent, inhibited catalyst and $C_{10}^+$ alpha-olefins, suffers from a particular problem which is linked to the high proportion of ethylene and to the sensitivity of alpha-olefins to temperature, which imposes a bottom temperature in the distillation zone of less than 250° C., preferably less than 200° C. This produces a distillation column head temperature which can be achieved industrially, but at high operating cost. For example, it is often below −30° C. when the distillation zone consists of a distillation column with a bottom temperature of 200° C., where the solvent is ortho-xylene and where the major portion of the ethylene contained in the feed is to be separated overhead.

SUMMARY OF THE INVENTION

The aim of the invention is to provide a solution to the problem described above where separation must be carried out by distillation of a mixture as described above in a distillation zone which is generally a distillation column. The solution which forms the object of the invention consists of deliberately adding supplemental 1-butene to the mixture to be separated which is preferably a mixture from an ethylene oligomerisation step, either into the mixture before separation by distillation, or directly into the column, preferably to the upper plates, or a portion into the mixture and the other portion directly into the column. Thus the bottom temperature of the column is maintained at a temperature at which the alpha-olefins are stable, and an effluent which principally contains the major portion of the ethylene contained in the mixture and possibly a portion of the 1-butene contained in the mixture can be separated overhead, while a mixture comprising all or a portion of the 1-butene, the alpha-olefins containing more than 6 carbon atoms per molecule, the hydrocarbon solvent and the inhibited catalyst can be separated at the bottom. The solution described above can be generalised to any case where a mixture of the same type must be separated by distillation, in a distillation zone which is generally a distillation column.

The importance of our solution is that a reasonable condensation temperature is obtained at the head of the column. The effluents obtained can be pumped into a higher pressure column in the separation train which is downstream of the distillation zone of the invention. This avoids the use of compressors which are more delicate than pumps as regards maintenance.

Thus the process of the invention is a process for the separation of a mixture comprising ethylene, a $C_4$ hydrocarbon cut, i.e., principally comprising hydrocarbons containing 4 carbon atoms per molecule, the major portion being comprised by 1-butene, a $C_6$ hydrocarbon cut, i.e., principally comprising hydrocarbons containing 6 carbon atoms per molecule, mainly comprising alpha-olefins containing at least 6 carbon atoms per molecule and possibly hydrocarbon products containing at least 7 carbon atoms per molecule, the ethylene content of the mixture being in the range 30% to 70% by weight, preferably in the range 40% to 60% by weight, in which separation is effected in a distillation zone to obtain an overhead fraction comprising the major portion of the ethylene present in the mixture and between 0% and 100% by weight, preferably between 50% and 70% by weight, and more preferably between 55% and 65% by weight of the 1-butene present in the mixture, the process being characterized in that the zone is also supplied with supplemental 1-butene in an amount in the range 1 to 40 times the quantity (by weight) of 1-butene present in the mixture, preferably in the range 2 to 25 times the quantity, and more preferably in the range 5 to 20 times the quantity.

The condensation temperature at the head of the distillation zone at reflux is generally in the range −35° C. to +60° C., preferably in the range +20° C. to +50° C.

The process of the invention comprises at least two possible implementations. In a first implementation of the process of the invention, supplemental 1-butene is added to the mixture before its entry into the distillation zone, and so the [mixture +supplemental 1-butene] total 1-butene is supplied to the zone. In a further implementation of the process of the invention, the supplemental 1-butene is injected directly into the distillation zone independently of the supply of the mixture, preferably to the upper plates of the zone. However, the scope of the invention also includes a third possibility which consists of combining the two preceding possibilities, i.e., a portion of the 1-butene is added to the mixture and the other portion is injected directly into the distillation zone.

In a preferred implementation of the process of the invention, the mixture originates from a homogeneous liquid ethylene oligomerisation zone and comprises unreacted ethylene, 1-butene, 1-hexene, 1-octene, olefins containing at least 10 carbon atoms per molecule, and oligomerisation solvent. Preferably, the mixture further comprises the oligomerisation catalyst which has been deactivated by an inhibitor, i.e., the inhibited catalyst. The inhibitor is generally selected from the group formed by amines, and preferably it is selected from the group formed by long chain amines, i.e., amines containing at least 6 carbon atoms per molecule.

The solvent is generally selected from compounds which are known to the skilled person for the activity as a solvent for ethylene oligomerisation. However, any other solvent which is known to the skilled person to have similar boiling point(s) and comparable properties could be envisaged. The solvent is generally a hydrocarbon, but a non hydrocarbon solvent could also be used. The solvent is preferably selected from hydrocarbon solvents containing at least one aromatic nucleus. More preferably, the solvent is principally constituted by a mixture of xylenes, and more preferably again, the solvent is ortho-xylene.

Within the scope of the preferred implementation of the invention, the process comprises a separation train downstream of the distillation zone, supplied by at least the major portion of the bottom product from the zone. The separation train can also be separately fed by the overhead product from the zone, especially when the overhead product includes 1-butene. The separation zone thus formed by the separation train and the distillation zone can effect different subsequent separations. Thus in a first implementation, it can produce an effluent comprising ethylene as its major portion, an effluent comprising 1-butene as its major portion, an effluent comprising 1-hexene and 1-octene as its major portion, and an effluent comprising alpha-olefins containing at least 10 carbon atoms per molecule as its major portion, along with inhibited catalyst and solvent. In a second implementation, it can produce an effluent comprising ethylene as its major portion, an effluent comprising 1-butene as its major portion, an effluent comprising 1-hexene as its major portion, an effluent comprising 1-octene as its major portion, and an effluent comprising alpha-olefins containing at least 10 carbon atoms per molecule as its major portion, along with inhibited catalyst and solvent. Finally, in a third implementation, it can produce an effluent comprising ethylene as its major portion, an effluent comprising 1-butene as its major portion, an effluent comprising 1-hexene as its major portion, an effluent comprising 1-octene as its major portion, an effluent comprising the solvent as its major portion, and an effluent comprising alpha-olefins containing at least 10 carbon atoms per molecule as its major portion, along with inhibited catalyst.

Within the context of the preferred implementation of the process of the invention and in accordance with the three variations described above, the process can produce at least one effluent comprising ethylene as its major portion, and preferably the process is such that the major portion of the portion of the effluent comprising ethylene as its major portion is recycled to the oligomerisation zone. In addition to ethylene, the portion can also comprise 0% to 20% by weight of 1-butene, preferably 3% to 10% by weight of 1-butene, i.e., it may contain no 1-butene at all or it may contain 1-butene in an amount of 0% to 20% by weight, preferably 3% to 10% by weight.

The following-non limiting example illustrates the invention.

EXAMPLE

A mixture originating from an oligomerisation step and comprising ethylene (771 kg/h) and alpha-olefins such as 1-butene (273 kg/h), 1-hexene (206 kg/h), 1-octene (112 kg/h) and oligomers containing at least ten carbon atoms per molecule (167 kg/h) was separated; the oligomerisation solvent was ortho-xylene (3712 kg/h) and the catalyst had been deactivated by the addition of dodecylamine. The distillation zone consisted of a distillation column in which the bottom temperature needed to be 200° C.

A pressure of 10.5 bars (1.05 MPa) and a condensation temperature at reflux of −50.3° C. were requirements for practically all of the ethylene contained in the feed to be separated. A pressure of 3.5 bars (0.35 MPa) and a condensation temperature at reflux of −73° C. were requirements for a mixture of olefins containing 2 to 8 carbon atoms per molecule to be separated. The two calculated condensation temperatures at reflux are hardly economical on an industrial scale.

Further, it was desired to produce a head temperature of 40° C. in the column, which was compatible with the use of a water condenser. Thus with the solution of the invention, which consisted of introducing 12 times the quantity of 1-butene contained in the mixture from the oligomerisation step into that mixture, the optimal pressure of the column was 29 bars (2.9 MPa) and the molar ratio of 1-butene in the overhead fraction was of the order of 50%.

We claim:

1. In a process for the separation of a mixture comprising: (a) ethylene, (b) a hydrocarbon cut principally comprising hydrocarbons containing 4 carbon atoms per molecule of which the major portion is 1-butene, (c) a hydrocarbon cut principally comprising hydrocarbons containing at least 6 carbon atoms per molecule of which the major portion consists of alpha-olefins containing at least 6 carbon atoms per molecule, the ethylene content of said mixture being in the range 30% to 70% by weight, said process comprising conducting the in separation in a distillation zone to obtain an overhead fraction and a bottoms fraction, the improvement comprising supplying said distillation zone with supplemental 1-butene in an amount in the range 1 to 40 times the quantity by weight of 1-butene present in said mixture and conducting the distillation so as to obtain an overhead fraction comprising the major portion of the ethylene present in said mixture and between 0% and 100% by weight of the total of both the 1-butene present in said mixture and in said supplemental 1-butene.

2. A process according to claim 1, in which the mixture further comprises hydrocarbon products containing at least 7 carbon atoms per molecule.

3. A process according to claim 1, in which the supplemental 1-butene is added to said mixture before its entry into the distillation zone, so that the total of the mixture and supplemental 1-butene [[mixture+supplemental 1-butene] ensemble] is supplied to said zone.

4. A process according to claim 1, in which the supplemental 1-butene is injected directly into the distillation zone independently of the supply of said mixture.

5. A process according to claim 1, in which a portion of the 1-butene is added to the mixture and the other portion of the 1-butene is injected directly into the distillation zone independently of the supply of said mixture.

6. A process according to claim 1, in which the mixture originates from a homogeneous liquid ethylene oligomerisation zone and comprises unreacted ethylene, 1-butene, 1-hexene, 1-octene, alpha-olefins containing at least 10 carbon atoms per molecule, inhibited oligomerisation catalyst.

7. A process according to claim 6 comprising a separation train downstream of the distillation zone, said separation train being supplied with the major portion of the product from the bottom of said zone, the separation zone thus constituted by said separation train and said distillation zone producing an effluent comprising ethylene as its major portion, an effluent comprising 1-butene as its major portion, an effluent comprising 1-hexene and 1-octene as its major portion, and an effluent comprising alpha-olefins containing at least 10 carbon atoms per molecule as its major portion, along with inhibited catalyst and solvent.

8. A process according to claim 6 comprising a separation train downstream of the distillation zone, said separation train being supplied with the major portion of the product from the bottom of said zone, the separation zone thus constituted by said separation train and said distillation zone being capable of producing an effluent comprising ethylene as its major portion, an effluent comprising 1-butene as its major portion, an effluent comprising 1-hexene as its major portion, an effluent comprising 1-octene as its major portion, and an effluent comprising compounds containing at least 10 carbon atoms per molecule as its major portion, along with inhibited catalyst and solvent.

9. A process according to claim 6 comprising a separation train downstream of the distillation zone, said separation train being supplied with the major portion of the product from the bottom of said zone, the separation zone thus constituted by said separation train and said distillation zone producing an effluent comprising ethylene as its major portion, an effluent comprising 1-butene as its major portion, an effluent comprising 1-hexene as its major portion, an effluent comprising 1-octene as its major portion, an effluent comprising the solvent as its major portion, and an effluent comprising alpha-olefins containing at least 10 carbon atoms per molecule as its major portion, along with inhibited catalyst.

10. A process according to claim 6, in which a major portion of the portion of the effluent comprising ethylene as its major portion is recycled to the oligomerisation zone.

11. A process according to claim 10, in which said recycled portion further comprises 0% to 20% by weight of 1-butene in addition to the ethylene.

12. A process according to claim 1, in which said overhead fraction comprises between 50% and 70% by weight of the 1-butene present in the total of the mixture and supplemental 1-butene.

13. A process according to claim 1, in which said overhead fraction comprises between 55% and 65% by weight of the 1-butene present in the total of the mixture and supplemental 1-butene.

14. A process according to claim 1, in which said supplemental 1-butene is supplied to the distillation zone in an amount in the range of 2 to 25 times the quantity by weight of 1-butene present in the mixture.

15. A process according to claim 1, in which said supplemental 1-butene is supplied to the distillation zone in an amount in the range of 5 to 20 times the quantity by weight of 1-butene present in the mixture.

16. A process according to claim 11, wherein said recycled portion contains 3–10% by weight of 1-butene.

17. A process according to claim 7, in which a major portion of the portion of the effluent comprising ethylene as its major portion is recycled to the oligomerisation zone.

18. A process according to claim 8, in which a major portion of the portion of the effluent comprising ethylene as its major portion is recycled to the oligomerisation zone.

19. A process according to claim 9, in which a major portion of the portion of the effluent comprising ethylene as its major portion is recycled to the oligomerisation zone.

20. A process according to claim 1, wherein the distillation is conducted in a column and overhead from the head of column has a condensation temperature of −35° C. to +60° C.

21. A process according to claim 20, wherein the condensation temperature is +20° C. to +50° C.

* * * * *